US012708327B2

(12) United States Patent
Galas et al.

(10) Patent No.: US 12,708,327 B2
(45) Date of Patent: Aug. 18, 2026

(54) METHOD AND SYSTEM TO COMPUTE HEMODYNAMIC PARAMETERS

(71) Applicant: GE Precision Healthcare LLC, Waukesha, WI (US)

(72) Inventors: Thierry Galas, Cherisy (FR); Theo Champion, Paris (FR); Charly Emmanuel Girot, Paris (FR)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 200 days.

(21) Appl. No.: 18/408,135

(22) Filed: Jan. 9, 2024

(65) Prior Publication Data

US 2025/0221670 A1 Jul. 10, 2025

(51) Int. Cl.

| | |
|---|---|
| ***A61B 5/00*** | (2006.01) |
| ***A61B 5/02*** | (2006.01) |
| ***A61B 5/026*** | (2006.01) |
| ***G06T 5/60*** | (2024.01) |
| ***G16H 30/20*** | (2018.01) |

(52) U.S. Cl.

CPC ........ *A61B 5/7267* (2013.01); *A61B 5/02028* (2013.01); *A61B 5/026* (2013.01); *G06T 5/60* (2024.01); *G16H 30/20* (2018.01)

(58) Field of Classification Search

CPC ... A61B 5/7267; A61B 5/02028; A61B 5/026; A61B 5/02125; A61B 5/0263; A61B 6/5217; A61B 6/507; G06T 5/60; G16H 30/20; G01R 33/56366

See application file for complete search history.

(56) References Cited

U.S. PATENT DOCUMENTS

| | | | | |
|---|---|---|---|---|
| 6,898,453 | B2 | 5/2005 | Lee | |
| 7,580,737 | B2 | 8/2009 | Wintermark et al. | |
| 8,908,939 | B2 * | 12/2014 | Bredno | A61B 6/507 382/128 |
| 9,949,650 | B2 | 4/2018 | Edic et al. | |
| 10,034,614 | B2 | 7/2018 | Edic et al. | |

(Continued)

FOREIGN PATENT DOCUMENTS

| | | |
|---|---|---|
| CN | 116361650 A | 6/2023 |
| EP | 1537824 A1 | 6/2005 |

(Continued)

OTHER PUBLICATIONS

Lawrence et al., “An Adiabatic Approximation to the Tissue Homogeneity Model for Water Exchange in the Brain: I. Theoretical Derivation”, Journal of Cerebral Blood Flow & Metabolism, vol. 18, Issue 12, Dec. 1998, pp. 1365-1377.

(Continued)

*Primary Examiner* — Oommen Jacob

(74) *Attorney, Agent, or Firm* — Fletcher Yoder, P.C.

(57) ABSTRACT

Methods and systems are described herein for hemodynamic parameter estimation. In certain embodiments, a set of perfusion data is acquired for a region of interest using an imaging system. An artery signal is obtained from the set of perfusion data. A tissue signal is obtained from the set of perfusion data. The artery signal and the tissue signal are provided as inputs to one or more neural networks to determine one or more hemodynamic parameters for the region of interest. The one or more neural networks are trained using one or more synthetic data.

19 Claims, 9 Drawing Sheets

(56) References Cited

U.S. PATENT DOCUMENTS

| | | | | |
|---|---|---|---|---|
| 10,186,056 | B2 | 1/2019 | Senzig et al. | |
| 10,674,986 | B2 | 6/2020 | Venugopal et al. | |
| 10,964,017 | B2 * | 3/2021 | Pack | G06T 7/0012 |
| 11,744,472 | B2 | 9/2023 | Zhao et al. | |
| 12,288,328 | B2 * | 4/2025 | Anzai | G06N 3/08 |
| 2011/0229003 | A1 * | 9/2011 | Yang | A61B 5/055 382/128 |
| 2012/0141005 | A1 * | 6/2012 | Djeridane | A61B 6/481 382/131 |
| 2015/0272448 | A1 * | 10/2015 | Fonte | A61B 5/0263 600/504 |
| 2016/0148372 | A1 * | 5/2016 | Itu | G16H 50/20 382/128 |
| 2016/0166209 | A1 * | 6/2016 | Itu | A61B 5/7278 600/408 |
| 2017/0220760 | A1 * | 8/2017 | Fonte | A61B 5/029 |
| 2017/0325770 | A1 | 11/2017 | Edic et al. | |
| 2018/0153495 | A1 * | 6/2018 | Itu | G06T 7/0012 |
| 2018/0303351 | A1 | 10/2018 | Mestha et al. | |
| 2019/0001001 | A1 | 1/2019 | Fitzgerald et al. | |
| 2019/0150764 | A1 * | 5/2019 | Arnold | G16H 15/00 |
| 2020/0297219 | A1 | 9/2020 | Mitra et al. | |
| 2021/0133960 | A1 * | 5/2021 | Vaz | G06T 7/11 |
| 2022/0082647 | A1 * | 3/2022 | Sharma | G06N 3/0895 |
| 2022/0175332 | A1 | 6/2022 | Haase | |
| 2023/0142152 | A1 | 5/2023 | Venugopal et al. | |
| 2023/0144624 | A1 | 5/2023 | Venugopal et al. | |
| 2023/0253110 | A1 * | 8/2023 | Scannell | G16H 50/20 705/2 |
| 2024/0062061 | A1 * | 2/2024 | Bone | A61B 6/507 |
| 2024/0193767 | A1 * | 6/2024 | Moulton | G06T 7/11 |
| 2024/0221151 | A1 * | 7/2024 | De La Rosa | G06T 7/0012 |
| 2025/0221670 | A1 * | 7/2025 | Galas | A61B 6/5217 |

FOREIGN PATENT DOCUMENTS

| | | | |
|---|---|---|---|
| WO | 0057777 | A1 | 10/2000 |
| WO | 2020150512 | A1 | 7/2020 |

OTHER PUBLICATIONS

Koh et al., "The Inclusion of Capillary Distribution in the Adiabatic Tissue Homogeneity Model of Blood Flow", Phys Med Biol. May 2001; 46(5):1519-38. doi: 10.1088/0031-9155/46/5/313.

Cuenod et al., "Perfusion and Vascular Permeability: Basic Concepts and Measurement in DCE-CT and DCE-MRI", Diagnostic and Interventional Imaging (2013), 94, 1187-1204.

Kenneth L. Zierler, M.D., "Theoretical Basis of Indicator-Dilution Methods for Measuring Flow and Volume", Circulation Research, vol. X, Mar. 1962, http://ahajournals.org on Dec. 15, 2023, 15 pages.

L. Axel, "Cerebral blood flow determination by rapid-sequence computed tomography: theoretical analysis", Radiology, vol. 137, No. 3, Dec. 1, 1980, https://doi.org/10.1148/radiology.137.3.7003648, 2 pages.

I.J. Fox, M.D., "History and Developmental Aspects of the Indicator-Dilution Technic", http://ahajournals.org on Dec. 15, 2023, University of Minnesota, Circulation Research, vol. X, Mar. 1962, 12 pages.

Johnson, et al., "A model for capillary exchange", American Journal of Physiology, https://doi.org/10.1152/ajplegacy.1966.210.6.1299, Published Online: Jun. 1, 1966, 3 pages.

Cenic et al., "Dynamic CT Measurement of Cerebral Blood Flow: A Validation Study", AJNR, Am J Neuroradiol 20:63-73, Jan. 1999, 12 pages.

Cenic et al., "A CT Method to Measure Hemodynamics in Brain Tumors: Validation and Application of Cerebral Blood Flow Maps", AJNR Am J Neuroradiol 2000, 21 (3) 462-470, https://www.ajnr.org/content/21/3/462, 10 pages.

Purdie et al., "Functional CT imaging of angiogenesis in rabbit VX2 soft-tissue tumour", IOPscience, Phys. Med. Biol., vol. 46, No. 12, Nov. 1, 2001, DOI 10.1088/0031-9155/46/12/307, 5 pages.

Aaron So et al., "Non-invasive assessment of functionally relevant coronary artery stenoses with quantitative CT perfusion: preliminary clinical experiences", European Radiology, Cardiac, Published: Sep. 21, 2011, 22, 39-50 (2012), 10 pages.

Aaron So et al., "Quantitative myocardial perfusion measurement using CT Perfusion: a validation study in a porcine model of reperfused acute myocardial infarction", Published: Jul. 29, 2011, 28, 1237-1248 (2012), 11 pages.

Stewart et al., "Hepatic perfusion in a tumor model using DCE-CT: an accuracy and precision study", IOPscience, Physics in Medicine & Biology, vol. 53, No. 16, Published Jul. 24, 2008, DOI 10.1088/0031-9155/53/16/003, 5 pages.

Kudo et al., "Differences in CT Perfusion Maps Generated by Different Commercial Software: Quantitative Analysis by Using Identical Source Data of Acute Stroke Patients", Radiology, vol. 254, No. 1, Dec. 14, 2009, https://doi.org/10.1148/radiol.254082000, 3 pages.

Kudo et al., "Accuracy and Reliability Assessment of CT and MR Perfusion Analysis Software Using a Digital Phantom", Radiology, vol. 267, No. 1, Apr. 1, 2013, https://doi.org/10.1148/radiol.12112618, 3 pages.

Boutelier et al., "Bayesian Hemodynamic Parameter Estimation by Bolus Tracking Perfusion Weighted Imaging", IEEE Transactions on Medical Imaging, vol. 31, Issue: 7, Jul. 2012, https://ieeexplore.ieee.org/document/6165368, 4 pages.

CN116361650 Machine Translation; 21 pages.

EP application 24221472.4 filed Dec. 19, 2024—extended Search Report issued May 9, 2025; 9 pages.

U.S. Appl. No. 18/134,774 filed Apr. 14, 2023, Venugopal.

* cited by examiner

METHOD AND SYSTEM TO COMPUTE HEMODYNAMIC PARAMETERS

BACKGROUND

The subject matter disclosed herein relates to the use of deep neural networks to obtain hemodynamic parameters by identifying a non-parametric model from computed tomography (CT) perfusion.

Non-invasive imaging technologies (e.g., computed tomography (CT), magnetic resonance imaging (MRI), ultrasonography (US), positron emission tomography (PET), single photon emission computed tomography (SPECT)) allow images of the internal structures or features of a patient or object to be obtained without performing an invasive procedure on the patient or object. In particular, such non-invasive imaging technologies rely on various physical principles (such as the differential transmission of X-rays through a target volume, the reflection of acoustic waves within the volume, the paramagnetic properties of different tissues and materials within the volume, the breakdown of targeted radionuclides within the body, and so forth) to acquire data and to construct images or otherwise represent the observed internal features of the patient/object.

By way of example, computed tomography (CT) perfusion is an imaging modality used to evaluate microcirculation in tissues. Computed tomography perfusion imaging allows determination of absolute regional measurements of hemodynamic parameters (e.g., blood flow (BF), blood volume (BV), mean transit time (MTT), time to maximum (TMAX)). Visually coded (e.g., color coded, gray scale, annotated, and so forth)) maps of these hemodynamic parameters (e.g., hemodynamic parametric maps) may be produced for comparison against normal values. Threshold or baseline values of these hemodynamic parameters may be established to monitor modifications in microcirculation, which may be used to characterize various pathologies, such as ischemia in organs (e.g., brain, myocardium, lung), tumors neo-vascularization state and changes, specific organs (e.g., liver, kidney, lung) characteristics, etc.

Generation of hemodynamic parametric maps from four dimensional (4D) computed tomography perfusion acquisition involves the use of a deconvolution algorithm to retrieve hemodynamic features from voxel-wise one dimensional (1D) temporal signals. However, current implementations (e.g., a parametric model of perfusion using a least squares (LSQ) regression) do not perform well and exhibit low signal to noise ratio. In addition, errors may be introduced by bad registration and/or by the superposition of the remains of a previous bolus. Hence there is a need for a better and more robust technique for generating and evaluating such hemodynamic maps and data.

SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

As discussed herein, techniques are described that relate to utilizing deep learning (DL) approaches to estimate hemodynamic parameters from four dimensional (4D) computed tomography perfusion data. In one embodiment, during a computed tomography acquisition, a series of images are acquired for a region of interest (e.g., a tissue), which include images taken before, during, and after an injection of a contrast agent (e.g., tracer bolus or marking blood with other way (e.g., ASL)) to the region of interest. Deep learning algorithms are trained using synthetic (e.g., simulated) data, which is generated based on the 4D computed tomography perfusion data, to obtain a residual impulse function Q(t) of the region of interest. The deep learning algorithms are also trained to reduce/mitigate the image non-idealities in the 4D computed tomography perfusion data. Neural networks trained in this manner are used to estimate the residual impulse function Q(t) of the region of interest, which is used to determine corresponding hemodynamic parameters of the region of interest.

In one embodiment, a method is provided for calculating hemodynamic parameters. In accordance with this embodiment, a set of perfusion data is acquired for a region of interest using an imaging system. An artery signal is obtained from the set of perfusion data. A tissue signal is obtained from the set of perfusion data. The artery signal and the tissue signal are provided as inputs to one or more neural networks to determine one or more hemodynamic parameters for the region of interest. The one or more neural networks are trained using synthetic data.

In accordance with further aspects, in such a method the set of perfusion data may comprise computed tomography (CT) perfusion data. Alternatively, in the other embodiments, the set of perfusion data may comprise magnetic resonance imaging (MRI) perfusion data, positron emission tomography (PET) perfusion data, single photon emission computed tomography (SPECT) data, or ultrasound imaging data. In the same or other embodiments, the one or more synthetic data are generated based on a defined ground truth model. In the same or other embodiments, the tissue signal is a convolution of the artery signal and a residual impulse function of the region of interest. In such an embodiment the one or more hemodynamic parameters may be determined from the residual impulse function. In the same or other embodiments, the one or more neural networks are trained to correct image non-idealities in the set of perfusion data. In the same or other embodiments, the one or more hemodynamic parameters comprise at least one of a blood flow (BF), a blood volume (BV), a mean transit time (MTT), or time to max (TMAX).

In a further embodiment, a system is provided. In accordance with this embodiment, the system comprises one or more processors and memory accessible by the one or more processors, and the memory stories instructions. The instructions, when executed by the one or more processors, cause the one or more processors to perform operations comprising: receiving a set of perfusion data acquired using an imaging system to image a region of interest; obtaining an artery signal from the set of perfusion data; obtaining a tissue signal from the set of perfusion data; and providing the artery signal and the tissue signal to serve as inputs to one or more neural networks to determine one or more hemodynamic parameters for the region of interest, wherein the one or more neural networks are trained using one or more synthetic data.

In accordance with further aspects, in such a system implementation the set of perfusion data may comprise computed tomography (CT) perfusion data. Alternatively, in the other embodiments, the set of perfusion data may comprise magnetic resonance imaging (MRI) perfusion data, positron emission tomography (PET) perfusion data, single photon emission computed tomography (SPECT) data, or ultrasound imaging data. In the same or other embodiments, the one or more synthetic data are generated based on a defined ground truth model. In the same or other embodiments, the tissue signal is a convolution of the artery signal and a residual impulse function of the region of interest. In such an embodiment the one or more hemodynamic parameters may be determined from the residual impulse function. In the same or other embodiments, the one or more neural networks are trained to correct image non-idealities in the set of perfusion data. In the same or other embodiments, the one or more hemodynamic parameters comprise at least one of a blood flow (BF), a blood volume (BV), a mean transit time (MTT), or a time to maximum (TMAX).

In an additional embodiment, a method is provided for training one or more neural networks. In accordance with this embodiment, a set of synthetic residual impulse functions for a region of interest is generated based on a defined ground truth model. An artery signal is obtained from a set of perfusion data. A synthetic tissue signal is generated based on the set of synthetic residual impulse function and the artery signal. The one or more neural networks are trained using a signal generated using the synthetic tissue signal and the artery signal.

In accordance with further aspects, in such a method the synthetic tissue signal may comprise a perturbation related to perturbating of the perfusion data. The perturbation may be associated with registration errors that may occur during perfusion data acquisitions (e.g., patient movements during acquisition) or may be associated with noise originating from the image acquisition technique being used (e.g., gaussian noise, artefacts, speckle noise, bolus superposition). In the same or other embodiments, the set of perfusion data may comprise computed tomography (CT) perfusion data. In the other embodiments, the set of perfusion data may comprise magnetic resonance imaging (MRI) perfusion data, positron emission tomography (PET) perfusion data, single photon emission computed tomography (SPECT) data, or ultrasound imaging data. In the same or other embodiments, a loss is used as a bias for the training of the one or more neural networks. In such an implementation the loss is determined based on a comparison of a first set of parameters derived from an estimated residual impulse function output from the one or more neural networks and a second set of parameters derived from the synthetic residual impulse function. The first set of parameters may comprise a first set of hemodynamic parameters and the second set of parameters may comprise a second set of hemodynamic parameters In the same or other embodiments, the training of the one or more neural networks is determined to be finished when the loss is less than a threshold or after a number of epochs. In the same or other embodiments, a regularization is used as a bias for the training of the one or more neural networks. In such an implementation the regularization is associated with characteristics of an estimated residual impulse function output from the one or more neural networks. In the same or other embodiments, the regularization may be weighted by the deconvolution error.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
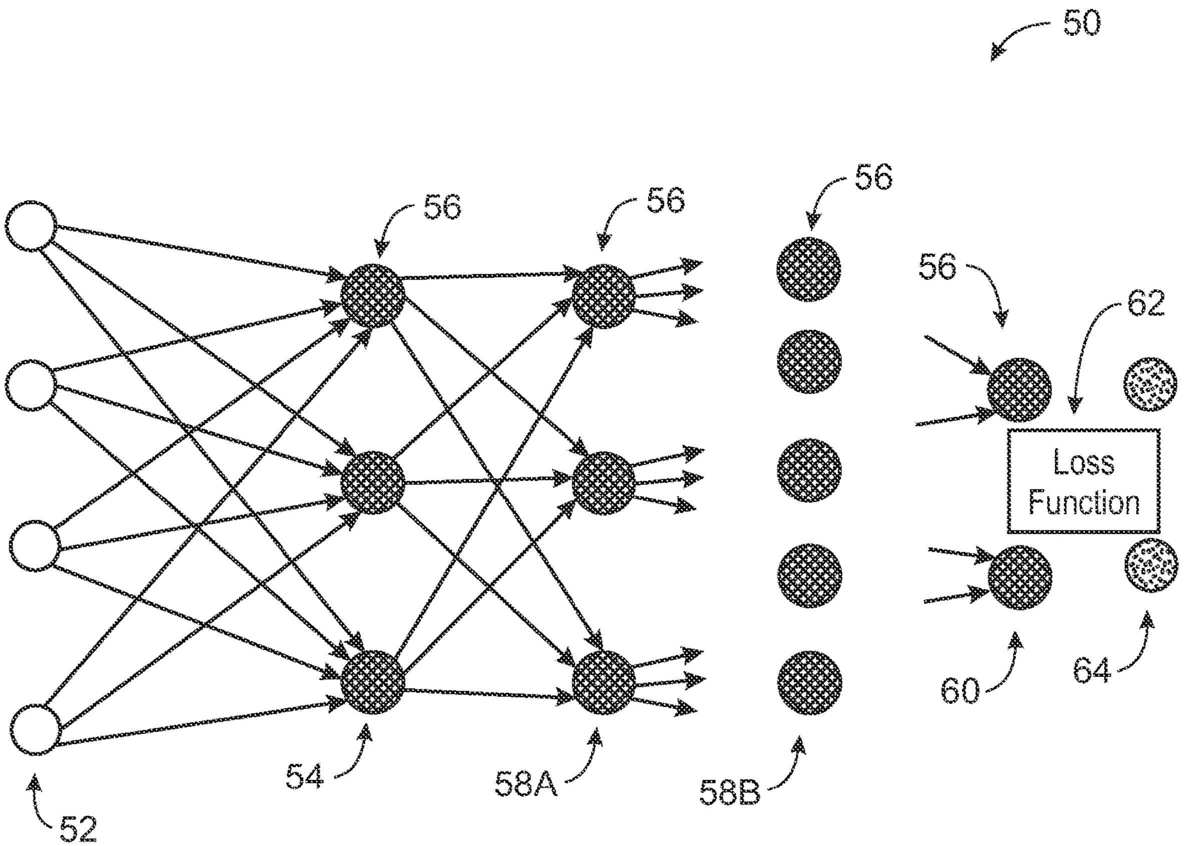
FIG. 1 depicts an example of an artificial neural network for training a deep learning model, in accordance with aspects of the present disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation specific decisions must be made to achieve the developers' specific goals, such as compliance with system related and business related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

While aspects of the following discussion are provided in the context of medical imaging, it should be appreciated that aspects of the disclosed techniques may be applicable to other contexts, and are thus not limited to such medical examples. Indeed, the provision of examples and explanations in such a medical context is only to facilitate explanation by providing instances of real world implementations and applications, and should therefore not be interpreted as limiting the applicability of the present approaches with respect to other applicable uses, such as for other non-destructive and/or non-invasive imaging contexts.

As discussed herein, perfusion imaging is an imaging modality that is used to evaluate microcirculation in tissues. Microcirculation is associated with supplying oxygen and nutrients (including drugs and toxins), removal of $CO_2$ and other metabolic waste products (e.g., catabolites, toxins), releasing and/or capturing mediators (e.g., hormones, neurotransmitters), producing the immune response and inflammation, regulating tissue fluids, temperature and core body temperature, controlling blood pressure, and so forth. Perfusion generally includes injection of a venous bolus of a contrast agent (e.g., a substance or composition that is used to enhance the visibility of a tissue (such as blood) or other media that might otherwise be difficult to observe in images generated using a given imaging modality) into a tissue and acquisition of multiple phases of the tissue after the bolus injection using an imaging modality, such as a computed tomography (CT) scanner. Computed tomography (CT) perfusion imaging allows absolute regional measurements of hemodynamic parameters (e.g., blood flow (BF), blood volume (BV), mean transit time (MTT), time to max (TMAX)). Color or other visually coded maps of these hemodynamic parameters (e.g., hemodynamic parametric maps) may be produced for comparison against normal or baseline values for the individual (e.g., longitudinal studies) or for a relevant population or sub-population. Threshold values of these hemodynamic parameters may be established to monitor modifications in microcirculation, which may be used to characterize various pathologies, such as ischemia in organs (e.g., brain, myocardium, lung), tumors neo-vascularization state and changes, specific organs (e.g., liver, kidney, lung) characteristics, etc. The computed tomography perfusion acquisition data may include three dimensional spatial data and one dimensional temporal data, which together constitute four dimensional (4D) computed tomography perfusion data. Generation of hemodynamic parametric maps from the four dimensional (4D) computed tomography perfusion acquisition involves the use of a deconvolution algorithm to retrieve hemodynamic features from voxel-wise one dimensional (1D) temporal signal. The present discussion is directed to using deep learning (DL) approaches to resolve the deconvolution algorithm and to generate the hemodynamic parametric maps or other comparable data outputs.

Although computed tomography (CT) examples are primarily provided herein, it should be understood that the disclosed technique may be used in other imaging modalities. For instance, the presently described approach may also be employed on data acquired by other types of tomographic scanners including, but not limited to, ultrasonography (US), positron emission tomography (PET), single photon emission computed tomography (SPECT), magnetic resonance imaging (MRI) scanners and/or other X-ray based imaging techniques, such as C-arm based techniques. The disclosed technique may also be used in the processing of computed tomography angiography (CTA) and perfusion combined acquisition.

By way of background, several imaging modalities, such as X-ray computed tomography (e.g., multi-slice CT, helical CT, cone beam CT) and X-ray C-arm systems (e.g., cone beam imaging), measure projections of the object or patient being scanned where the projections, depending on the technique, correspond to Radon transform data, fan beam transform data, cone beam transform data, or non-uniform Fourier transforms. In other contexts, the scan data may be magnetic resonance data (e.g., magnetic resonance imaging (MRI) data) generated in response to applied magnetic fields and RF pulses, and so forth.

In other contexts, single photon emission computed tomography (SPECT) and positron emission tomography (PET) may utilize a radiopharmaceutical that is administered to a patient and whose breakdown results in the positron emission of gamma rays from locations within the patient's body. The radiopharmaceutical is typically selected so as to be preferentially or differentially distributed in the body based on the physiological or biochemical processes in the body. For example, a radiopharmaceutical may be selected that is preferentially processed or taken up by tumor tissue. In such an example, the radiopharmaceutical will typically be disposed in greater concentrations around tumor tissue within the patient.

In other contexts, an ultrasound imaging system may acquire ultrasound data of a patient. In certain embodiments, the ultrasound system may be a digital acquisition and beam former system, but in other embodiments, the ultrasound system may be any suitable type of ultrasound system. Such an ultrasound system may include the ultrasound probe and a workstation (e.g., monitor, console, user interface) which may control operation of the ultrasound probe and may process image data acquired by the ultrasound probe. The ultrasound probe may be coupled to the workstation by any suitable technique for communicating image data and control signals between the ultrasound probe and the workstation such as a wireless, optical, coaxial, or other suitable connection.

Reconstruction routines and related correction and calibration routines are employed in conjunction with these imaging modalities to generate useful clinical images and/or data, which in turn may be used to derive or measure hemodynamic parameters of interest, such as by using deep learning (DL) techniques, as discussed herein.

Deep learning (DL) approaches discussed herein may be based on artificial neural networks, and may therefore encompass one or more of deep neural networks, such as convolutional neural networks (CNNs), recurrent neural networks (RNNs), transformers, generative adversarial networks (GANs), and so forth. As discussed herein, deep learning techniques (which may also be known as deep machine learning, hierarchical learning, or deep structured learning) are a branch of machine learning techniques that employ mathematical representations of data and artificial neural networks for learning and processing such representations. Neural networks may include multiple layers, such as input layers, hidden layers, and output layers. The basic unit of computation in a neural network is the neuron/node. Each neuron/node receives inputs from some other nodes, or from an external source and computes outputs. The input layer may include neurons/nodes to receive external inputs, such as input data. Each hidden layer is made up of a set of neurons/nodes that have learnable weights and biases, and each neuron/node in the hidden layers may receive inputs from upstream connected nodes or layers and perform operations on the inputs to compute outputs that are provided to downstream connected nodes or layers. The output layer may include neurons/nodes to receive inputs from the hidden layers and output results.

By way of example, deep learning (DL) approaches may be characterized by their use of one or more algorithms to extract or model high level abstractions of a type of data of interest. This may be accomplished using one or more processing layers, with each layer typically corresponding to a different level of abstraction and, therefore potentially employing or utilizing different aspects of the initial data or outputs of a preceding layer (i.e., a hierarchy or cascade of layers) as the target of the processes or algorithms of a given layer. In an image processing or reconstruction context, this may be characterized as different layers corresponding to the different feature levels or resolution in the data. In general, the processing from one representation space to the next level representation space can be considered as one 'stage' of the process. Each stage of the process can be performed by separate neural networks or by different parts of one larger neural network.

With this in mind, the techniques discussed herein utilize deep learning (DL) approaches to estimate hemodynamic parameters from the computed tomography perfusion data. In certain of the implementations discussed herein, deep learning algorithms are trained using synthetic (e.g., simulated) data generated based on clinical data as training data, as opposed to clinical, real world data or geometric constructs. The use of synthetic data for training one or more deep learning algorithms, as discussed herein, is in contrast to the direct use of clinical data for such training purposes, which may involve either estimation of the ground truth state or the acquisition of additional data that is representative of the ground truth state and the registration of the additional data to the clinical data to assemble the training data.

As discussed herein, as part of the initial training of deep learning processes to solve a particular problem, training data sets may be employed that have known initial values and known (i.e., ground truth) values for a final output of the deep learning process. In this manner, the ground truth training data may be used to train a network to provide the known correct outputs in response to the known inputs. As discussed in greater detail below, in accordance with the present approach, the synthetic data is used as training data, where the synthesized data is simulated or synthesized or derived from clinical data and/or simple geometric constructs, but is distinct from the clinical data. Further, due to their synthetic nature, the synthetic training data discussed herein are associated with known ground truth properties, without having to estimate or measure such ground truths or perform additional invasive operations to derive such ground truth properties.

For example, the training of a single stage may have known input values corresponding to one representation space and known output values corresponding to a next level representation space. In this manner, the deep learning algorithms may process (either in a supervised or guided manner or in an unsupervised or unguided manner) the known or training data sets until the mathematical relationships between the initial data and desired output(s) are discerned and/or the mathematical relationships between the inputs and outputs of each layer are discerned and characterized. Similarly, separate validation data sets may be employed in which both the initial and desired target values are known, but only the initial values are supplied to the trained deep learning algorithms, and the outputs of the deep learning algorithm are compared to the desired target values to validate the prior training and/or to prevent over training.

With the preceding in mind, FIG. 1 schematically depicts an example of an artificial neural network 50 that may be trained as a deep learning model as discussed herein. In this example, the network 50 is multi-layered, with a training input 52 (e.g., synthetic data) and multiple layers including an input layer 54, hidden layers 58A, 58B, and so forth, and an output layer 60 and the training target 64 present in the network 50. In certain implementations, the input layer 54 may also be characterized as or understood to be a hidden layer. Each layer, in this example, is composed of a plurality of "neurons" or nodes 56. The number of neurons 56 may be constant between layers or, as depicted, may vary from layer to layer. Neurons 56 at each layer generate respective outputs that serve as inputs to the neurons 56 of the next hierarchical layer. In practice, a weighted sum of the inputs with an added bias is computed to "excite" or "activate" each respective neuron of the layers according to an activation function, such as rectified linear unit (ReLU), sigmoid function, hyperbolic tangent function, or otherwise specified or programmed function. The outputs of the final layer constitute the network output 60 which, in conjunction with a target image or parameter set 64, are used by loss or error function 62 to generate an error signal, which will be backpropagated to guide the network training.

The loss or error function 62 measures the difference between the network output and the training target. In certain implementations, the loss function may be the mean squared error (MSE) of the voxel level values or partial line integral values and/or may account for differences involving other image features, such as image gradients or other image statistics. Alternatively, the loss function 62 could be defined by other metrics associated with the particular task in question, such as a softmax function or DICE value (where DICE refers to the ratio $$\frac{2*(A\cap B)}{|A|+|B|},$$

with $A \cap B$ denoting the intersection of regions A and B, and $|\cdot|$ denoting the area of the region.)

To facilitate explanation of the present approach using deep learning techniques, the present disclosure primarily discusses these approaches in the context of a CT or C-arm systems. However, it should be understood that the following discussion may also be applicable to other image modalities and systems including, but not limited to, multi-spectral CT and MRI, as well as to any context where tomographic reconstruction is employed to reconstruct an image from which hemodynamic parameters may be discerned and/or measured.

Figure 2:
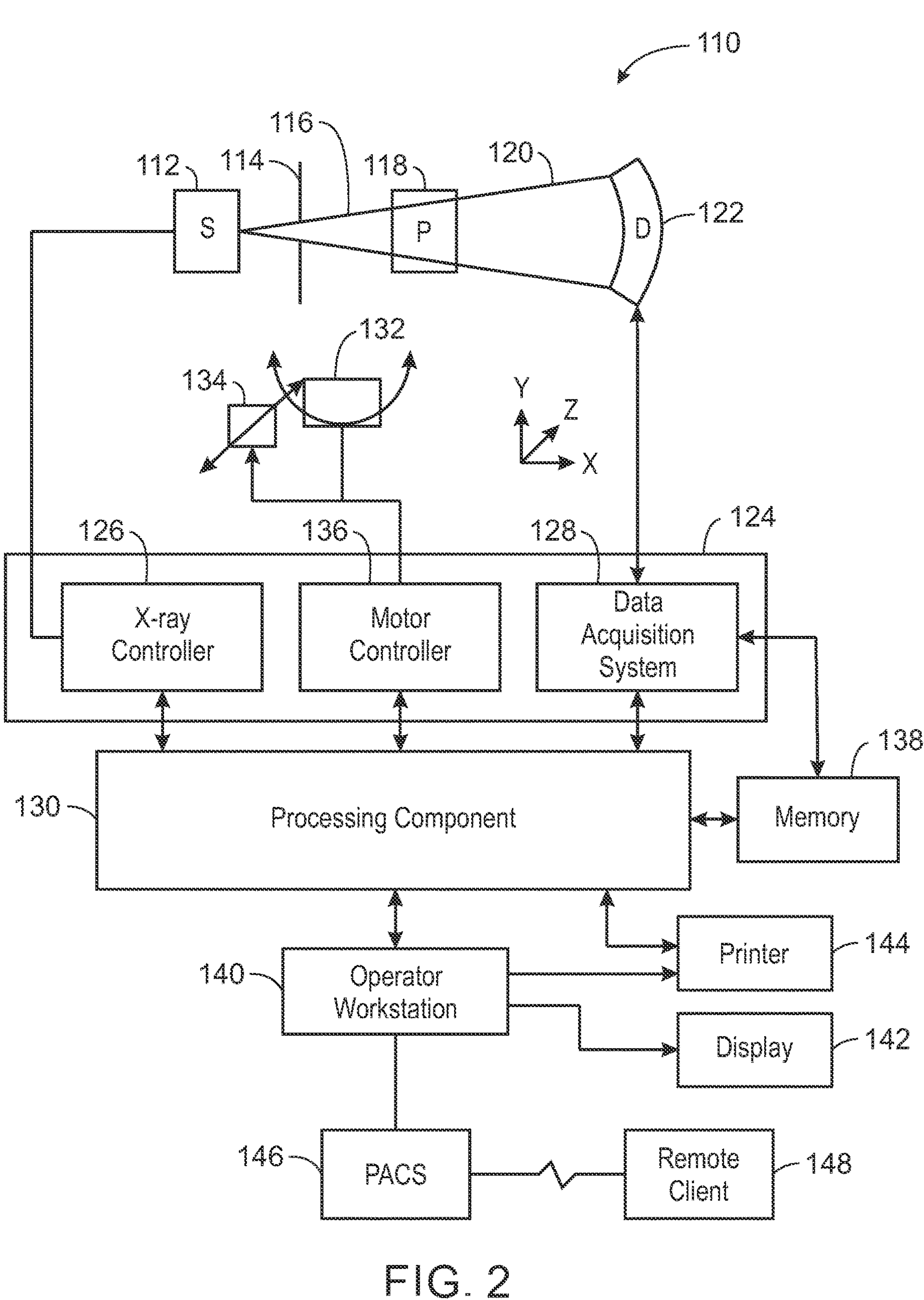
FIG. 2 is a block diagram depicting components of a computed tomography (CT) imaging system, in accordance with aspects of the present disclosure.

With this in mind, an example of an imaging system 110 (i.e., a scanner) is depicted in FIG. 2. In the depicted example, the imaging system 110 is a computed tomography imaging system designed to acquire scan data (e.g., X-ray attenuation data) at a variety of radial views around a patient (or other subject or object of interest) and suitable for performing image reconstruction using tomographic reconstruction techniques. In the embodiment illustrated in FIG. 2, imaging system 110 includes a source of X-ray radiation 112 positioned adjacent to a collimator 114. The X-ray source 112 may be an X-ray tube, a distributed X-ray source (such as a solid-state or thermionic X-ray source) or any other source of X-ray radiation suitable for the acquisition of medical or other images. Conversely, MRI embodiments the measurements are samples in Fourier space and can either be applied directly as the input to the neural network or can first be converted to line integrals in sinogram space.

In the depicted example, the collimator 114 shapes or limits a beam of X-rays 116 that passes into a region in which a patient/object 118 is positioned. In the depicted example, the X-rays 116 are collimated to be a cone shaped beam (i.e., a cone beam) or a fan shaped beam (i.e., a fan beam) that passes through the imaged volume. A portion of the X-ray radiation 120 passes through or around the patient/object 118 (or other subject of interest) and impinges on a detector array, represented generally at reference numeral 122. Detector elements of the array produce electrical signals that represent the intensity of the incident X-rays 120. These signals are acquired and processed to reconstruct images of the features within the patient/object 118.

Source 112 is controlled by a system controller 124, which furnishes both power, and control signals for computed tomography examination sequences. In the depicted embodiment, the system controller 124 controls the source

112 via an X-ray controller 126 which may be a component of the system controller 124. In such an embodiment, the X-ray controller 126 may be configured to provide power and timing signals to the X-ray source 112.

Moreover, the detector 122 is coupled to the system controller 124, which controls acquisition of the signals generated in the detector 122. In the depicted embodiment, the system controller 124 acquires the signals generated by the detector using a data acquisition system 128. The data acquisition system 128 receives data collected by readout electronics of the detector 122. The data acquisition system 128 may receive sampled analog signals from the detector 122 and convert the data to digital signals for subsequent processing by a processing component 130 discussed below. Alternatively, in other embodiments, the digital to analog (DAC) conversion may be performed by circuitry provided on the detector 122 itself. The system controller 124 may also execute various signal processing and filtration functions with regard to the acquired signals, such as for initial adjustment of dynamic ranges, interleaving of digital data, and so forth.

In the embodiment illustrated in FIG. 2, system controller 124 is coupled to a rotational subsystem 132 and a linear positioning subsystem 134. The rotational subsystem 132 enables the X-ray source 112, collimator 114 and the detector 122 to be rotated one or multiple turns around the patient/object 118, such as rotated primarily in an x,y plane about the patient. It should be noted that the rotational subsystem 132 might include a gantry or C-arm upon which the respective X-ray emission and detection components are disposed. Thus, in such an embodiment, the system controller 124 may be utilized to operate the gantry or C-arm.

The linear positioning subsystem 134 may enable the patient/object 118, or more specifically a table supporting the patient, to be displaced within the bore of the CT system 110, such as in the z-direction relative to rotation of the gantry. Thus, the table may be linearly moved (in a continuous or step-wise fashion) within the gantry to generate images of particular regions of interest of the patient 118. In the depicted embodiment, the system controller 124 controls the movement of the rotational subsystem 132 and/or the linear positioning subsystem 134 via a motor controller 136.

In general, system controller 124 commands operation of the imaging system 110 (such as via the operation of the source 112, detector 122, and positioning systems described above) to execute examination protocols, such as a computed tomography perfusion protocol, and to process acquired data. For example, the system controller 124, via the systems and controllers noted above, may rotate a gantry supporting the source 112 and detector 122 about a subject of interest so that X-ray attenuation data may be obtained at one or more angular positions relative to the subject. In the present context, system controller 124 may also include signal processing circuitry, associated memory circuitry for storing programs and routines executed by the computer (such as routines for performing vascular property estimation techniques described herein), as well as configuration parameters, image data, and so forth.

In the depicted embodiment, the signals acquired and processed by the system controller 124 are provided to a processing component 130, which may perform image reconstruction. The processing component 130 may be one or more general or application specific microprocessors. The data collected by the data acquisition system 128 may be transmitted to the processing component 130 directly or after storage in a memory 138. Any type of memory suitable for storing data might be utilized by such an exemplary system 110. For example, the memory 138 may include one or more optical, magnetic, and/or solid state memory storage structures. Moreover, the memory 138 may be located at the acquisition system site and/or may include remote storage devices for storing data, processing parameters, and/or routines for tomographic image reconstruction, as described below.

The processing component 130 may be configured to receive commands and scanning parameters from an operator via an operator workstation 140, typically equipped with a keyboard and/or other input devices. An operator may control the system 110 via the operator workstation 140. Thus, the operator may observe the reconstructed images and/or otherwise operate the system 110 using the operator workstation 140. For example, a display 142 coupled to the operator workstation 140 may be utilized to observe the reconstructed images and to control imaging. Additionally, the images may also be printed by a printer 144 which may be coupled to the operator workstation 140.

Further, the processing component 130 and operator workstation 140 may be coupled to other output devices, which may include standard or special purpose computer monitors and associated processing circuitry. One or more operator workstations 140 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

It should be further noted that the operator workstation 140 may also be coupled to a picture archiving and communications system (PACS) 146. PACS 146 may in turn be coupled to a remote client 148, radiology department information system (RIS), hospital information system (HIS) or to an internal or external network, so that others at different locations may gain access to the raw or processed image data. By way of example, in the present context a previously or recently acquired computed tomography perfusion image or image set may be subsequently accessed from such an archiving system for processing in accordance with the techniques discussed here for hemodynamic property estimation or longitudinal tracking.

While the preceding discussion has treated the various exemplary components of the imaging system 110 separately, these various components may be provided within a common platform or in interconnected platforms. For example, the processing component 130, memory 138, and operator workstation 140 may be provided collectively as a general or special purpose computer or workstation configured to operate in accordance with the aspects of the present disclosure. In such embodiments, the general or special purpose computer may be provided as a separate component with respect to the data acquisition components of the system 110 or may be provided in a common platform with such components. Likewise, the system controller 124 may be provided as part of such a computer or workstation or as part of a separate system dedicated to image acquisition.

The system of FIG. 2 may be utilized to acquire X-ray projection data (or other scan data for other modalities) for a variety of views about a vascularized region of interest of a patient to reconstruct images (e.g., perfusion images or maps) of the imaged region using the scan data. Projection (or other) data acquired by a system such as the imaging system 110 may be reconstructed as discussed herein to perform a tomographic reconstruction. Although the system of FIG. 2 shows a rotational subsystem 132 for rotating the X-ray source 112 and detector 122 about an object or subject, such a rotational subsystem may encompass non-planar rotational aspects (e.g., complex rotational trajectories or other motion including motion in other dimensions so as not to be strictly rotational within a single plane), such as may be suitable for use with certain C-arm type imaging systems.

Figure 3:
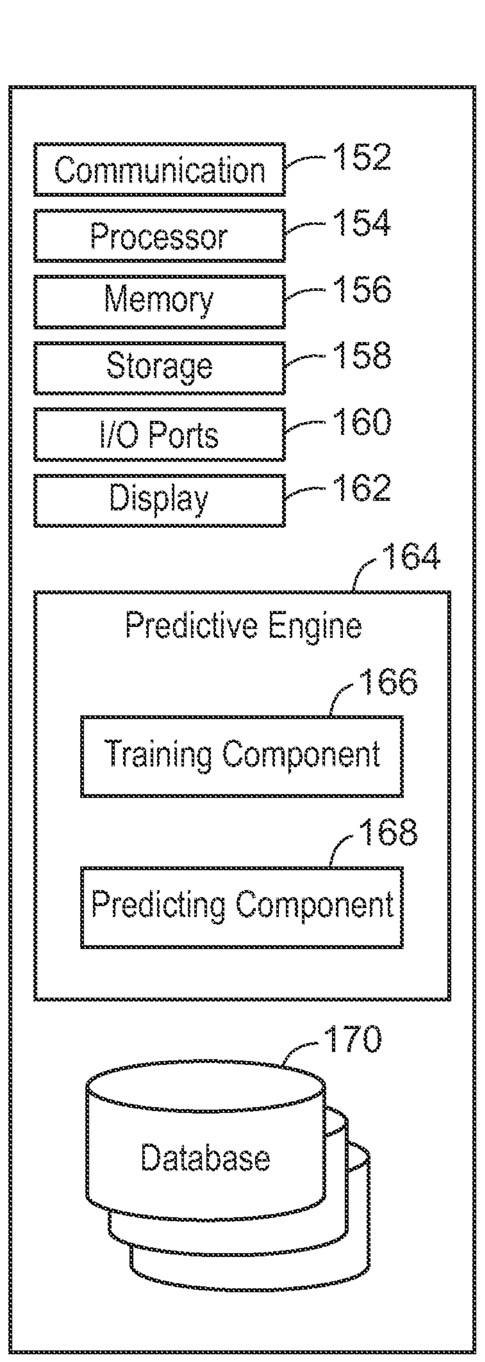
FIG. 3 depicts a block diagram of a computing system used to analyze images obtained from the computed tomography imaging system of FIG. 2, in accordance with aspects of the present disclosure.

FIG. 3 is a block diagram showing a computing system 150 that may be used in the remote client 148. Although the following description details some example components that make up the computing system 150, it should be understood that the computing system 150 may include additional or fewer components. The computing system 150 may include a communication component 152, a processor 154, a memory 156, a storage 158, input/output (I/O) ports 160, a display 162, and the like. The communication component 152 may be a wireless or wired communication component that may facilitate communication between the computing system 150 and various types of devices or resources (e.g., a database, a server) directly or via a network. Additionally, the communication component 152 may facilitate data transfer to the computing system 150, such that the computing system 150 may receive data from the components depicted in FIG. 2 (e.g., the PACS 146), and the like. The communication component 152 may use a variety of communication protocols, such as Open Database Connectivity (ODBC), TCP/IP Protocol, Distributed Relational Database Architecture (DRDA) protocol, Database Change Protocol (DCP), HTTP protocol, other suitable current or future protocols, or combinations thereof.

The processor 154 may include single threaded processor(s), multi-threaded processor(s), or both. The processor 154 may process instructions stored in the memory 156. The processor 154 may also include hardware based processor(s) each including one or more cores. The processor 154 may include general purpose processor(s), special purpose processor(s), or both. The processor 154 may be communicatively coupled to other internal components (such as the communication component 152, the storage 158, the I/O ports 160, and the display 162).

The memory 156 and the storage 158 may be any suitable articles of manufacture that can serve as media to store processor executable code, data, or the like. These articles of manufacture may represent computer readable media (e.g., any suitable form of memory or storage) that may store the processor executable code used by the processor 154 to perform the presently disclosed techniques. As used herein, applications may include any suitable computer software or program that may be installed onto the computing system 150 and executed by the processor 154. The memory 156 and the storage 158 may represent non-transitory computer readable media (e.g., any suitable form of memory or storage) that may store the processor executable code used by the processor 154 to perform various techniques described herein. It should be noted that non-transitory merely indicates that the media is tangible and not a signal.

The I/O ports 160 may be interfaces that may couple to other peripheral components such as input devices (e.g., keyboard, mouse), sensors, input/output (I/O) modules, and the like. The display 162 may operate as a human machine interface (HMI) to depict visualizations associated with software or executable code being processed by the processor 154. The display 162 may operate to depict a representation of the three dimensional (3D) augmented reality (AR) or virtual reality (VR) visualizations associated with software or executable code being processed by the processor 154. In one embodiment, the display 162 may be a touch display capable of receiving inputs from an operator of the computing system 150. The display 162 may be any suitable type of display, such as a liquid crystal display (LCD), plasma display, or an organic light emitting diode (OLED) display, for example. Additionally, in one embodiment, the display 162 may be provided in conjunction with a touch sensitive mechanism (e.g., a touch screen) that may function as part of a control interface for the computing system 150.

The computer system 150 may also include a predictive engine 164, which may include a training component 166 and a predicting component 168. The training component 166 may receive the training data (e.g., synthetic data) stored in a database 170 and use the training data to train a machine learning model. For example, a deep learning (DL) model may be trained with a supervised or guided manner (e.g., trained with training data that includes input data and desired predictive output (e.g., labeled dataset)). The deep learning model may also be trained with unsupervised or unguided manner (e.g., trained with training data that includes input data but without desired predictive output (e.g., unlabeled dataset)). The predicting component 168 may use a set of machine learning models (e.g., functions, algorithms) trained by the training data to predict outputs (e.g., hemodynamic parameters) for initial values (e.g., clinical data) supplied to the predicting component 168. In some embodiments, the predicted outputs may be supervised (e.g., by a user) to monitor or confirm the accuracy of the outputs, and the training data may be updated, which may be used by the training component 166 to retrain the machine learning model. The predictive engine 164 and/or the database 170 may be located in a local environment of the remote client 148 or in a cloud computing environment (e.g., a data center).

Figure 4:
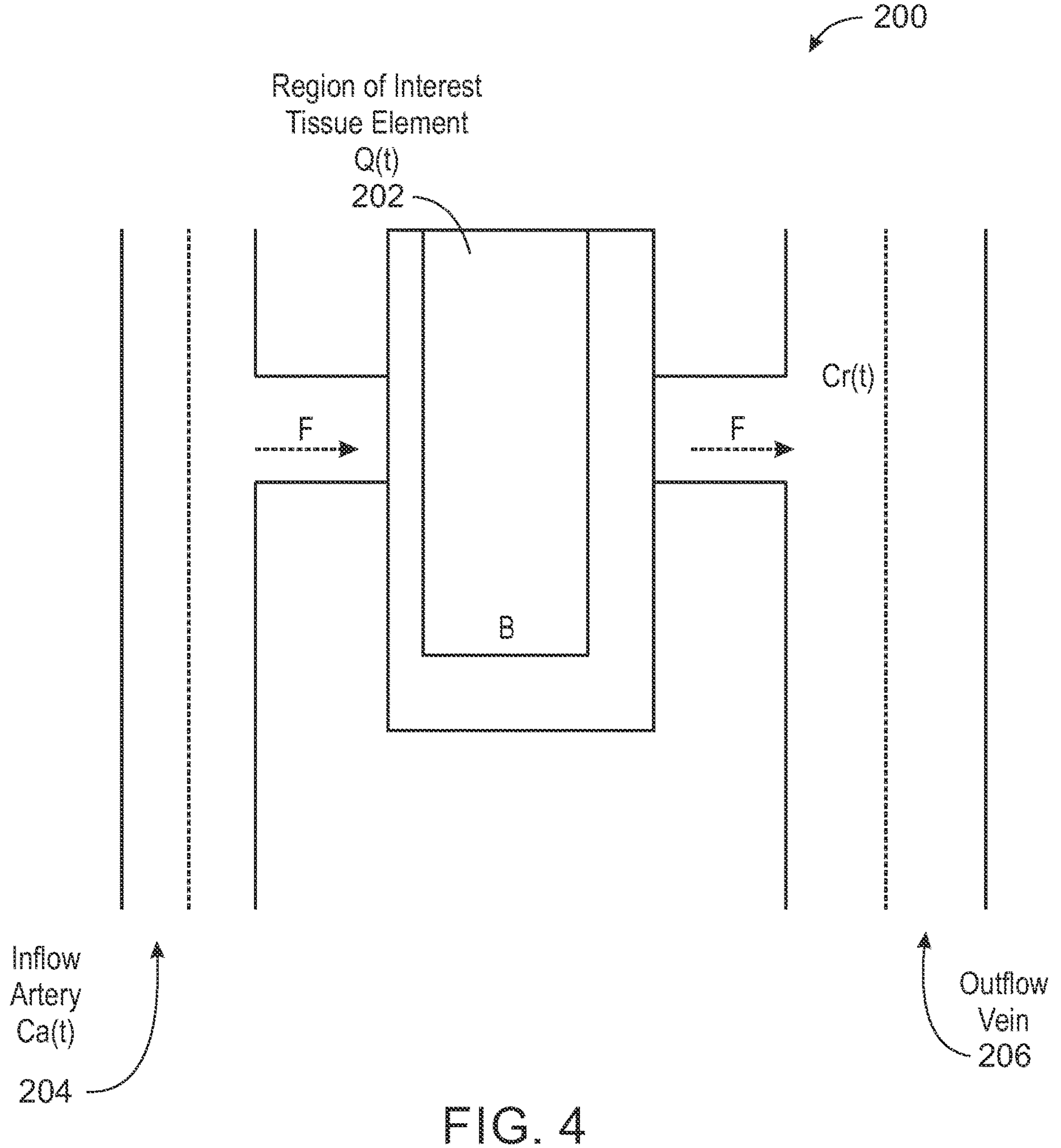
FIG. 4 depicts a rendering of a simplified indicator dilution physical model, in accordance with aspects of the present disclosure.

With the preceding background and context discussion in mind, the present disclosure relates to using deep learning approaches to estimate hemodynamic parameters from 4D computed tomography perfusion data. As mentioned previously, computed tomography (CT) perfusion generally includes injection of a venous bolus of a contrast agent into a tissue and acquisition of multiple phases of the tissue after the bolus injection using a computed tomography (CT) scanner. To measure the response of the tissue after the bolus injection, indicator dilution techniques have been used in physiological measurements. FIG. 4 is a block diagram of a simplified indicator dilution physical model 200 used to illustrate the computed tomography perfusion process. In the simplified indicator dilution physical model 200, a constant flow F of liquid runs from an inflow 204 (e.g., artery) to an outflow 206 (e.g., vein) through an internal compartment B of the region of interest 202. The dilution of indicator in the inflow 204 (e.g., artery) is indicated by an artery signal $C_a(t)$, and the response of the region of interest 202 to a unitary pulse of tracer in the inflow 204 is indicated by a residual impulse function Q(t). The response of the region of interest 202 to the artery signal $C_a(t)$ is indicated by a tissue signal $C_r(t)$ in the outflow 206 (e.g., vein). The tissue signal $C_r(t)$ is a convolution of the artery signal $C_a(t)$ and the residual impulse function Q(t), as illustrated in Equation (1).

$$C_r(t) = C_a(t) \otimes Q(t) \tag{1}$$

Accordingly, the residual impulse function Q(t) may be obtained by deconvolution of the tissue signal $C_r(t)$ based on Equation (1). The residual impulse function Q(t) may be used to obtain hemodynamic parameters of the region of interest 202, such as blood flow (BF), blood volume (BV), mean transit time (MTT), time to maximum (TMAX) etc. The tissue blood flow (BF) corresponds to the blood flow entering/exiting a volume of tissue (e.g., expressed in ml/min/100 ml). The blood volume (BV) corresponds to the volume of capillary blood contained in a certain volume of tissue (e.g., expressed in ml/100 ml or in %). The MTT is the mean time taken by blood to pass through the capillary network (time between the arterial inflow and venous outflow) (expressed in second). The artery signal $C_a(t)$ and the tissue signal $C_r(t)$ may be obtained from computed tomography scan acquisitions or measurements using other imaging modalities (e.g., MRI). For example, during a computed tomography acquisition, a series of images may be acquired for the region of interest 202, which may include images taken before the injection of a contrast agent (e.g., tracer bolus or marking blood with other way (e.g., ASL)), during the injection of the contrast agent, and after the injection of the contrast agent. Thus the computed tomography perfusion acquisition data may include three dimensional spatial data and one dimensional temporal data, which together constitute four dimensional (4D) computed tomography perfusion data. The series of images may be used to study the microcirculation during the bolus injection of the contrast agent. For example, the images acquired before the injection of the contrast agent may be used as reference or baseline images, and the images acquired during and after the injection of the contrast agent may be used to study the effect of the injection relative to the reference or baseline. Accordingly, changes of the residual impulse function Q(t) and the tissue signal $C_r(t)$ due to the injection of the contrast agent may be obtained from the series of images acquired in the computed tomography acquisition.

Figure 5:
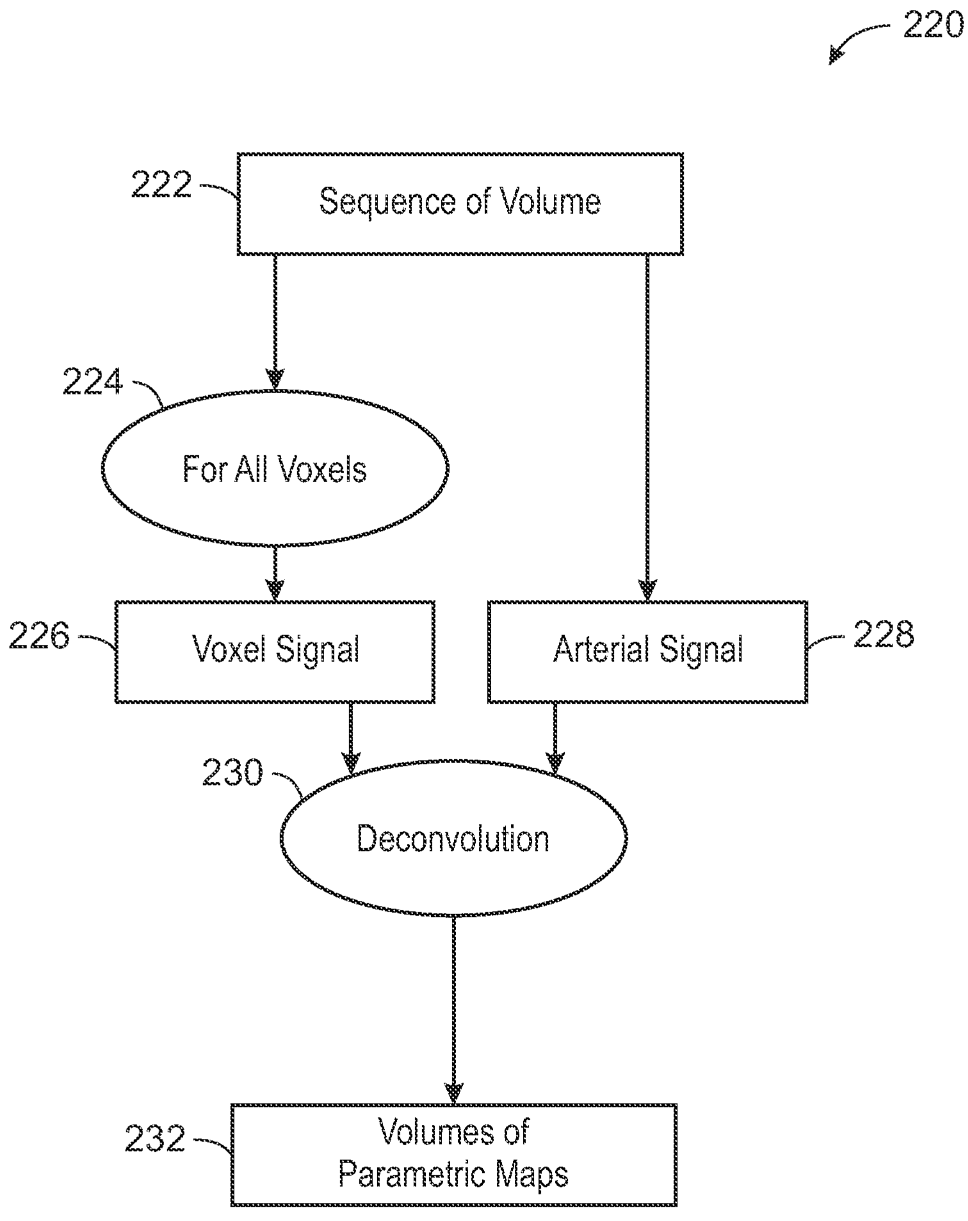
FIG. 5 depicts a flow chart illustrating a method to obtain a residual impulse function and corresponding hemodynamic parameters for a region of interest, in accordance with aspects of the present disclosure.

FIG. 5 is a flow chart illustrating a method 220 to obtain a residual impulse function Q(t) and corresponding hemodynamic parameters for a region of interest. At block 222, a sequence of volume may be obtained by using a series of images acquired using various modalities (e.g., CT, MR, and so forth) for the region of interest. As mentioned previously, the series of images may include images acquired before, during, and after intravenous injection of a contrast agent (e.g., tracer bolus or marking blood with other way (e.g., ASL)). For example, a sequential acquisition may be performed at the level of a slice or volume before, during, and after the injection of the contrast agent, and the images acquired before the start of the injection of the contrast agent may be used as reference images. These images may be segmented to produce a geometric representation of the true underlying lumen geometry. Segmentation of geometric features, such as plaque components, adjoining structures, and so forth, is envisioned. These geometric representations can be voxelized (converted to or represented by volumetric representations where each voxel corresponds to a particular tissue type or combination of tissue types based on the voxel's location relative to the geometric representation), or characterized by polygonal surfaces, NURBS (non-uniform rational b-splines), or any number of other representations. These representations may not exactly match the original shapes of the true lumen due to noise, resolution limits, and other image non-idealities, but they are sufficiently close that when taken together, a large series of these representations extracted from a large set of corresponding images may be representative of the geometric features commonly found in clinical practice. At block 224, tissue signals may be obtained for all voxels of the sequence of volume using the volumetric representations produced in block 222. At block 226, a sample tissue time signal may be obtained for a voxel or a small space area in the sequence of volume. At block 228, an arterial signal may be obtained from the series of images acquired at block 222. Then at block 230, a residual impulse function Q(t) of the voxel or the small space area may be obtained by deconvolution of the sample tissue time signal against the arterial signal based on Equation (1). At block 232, the result of the deconvolution may be used to obtain values of parametric maps in the corresponding voxel/small space area.

Figure 6:
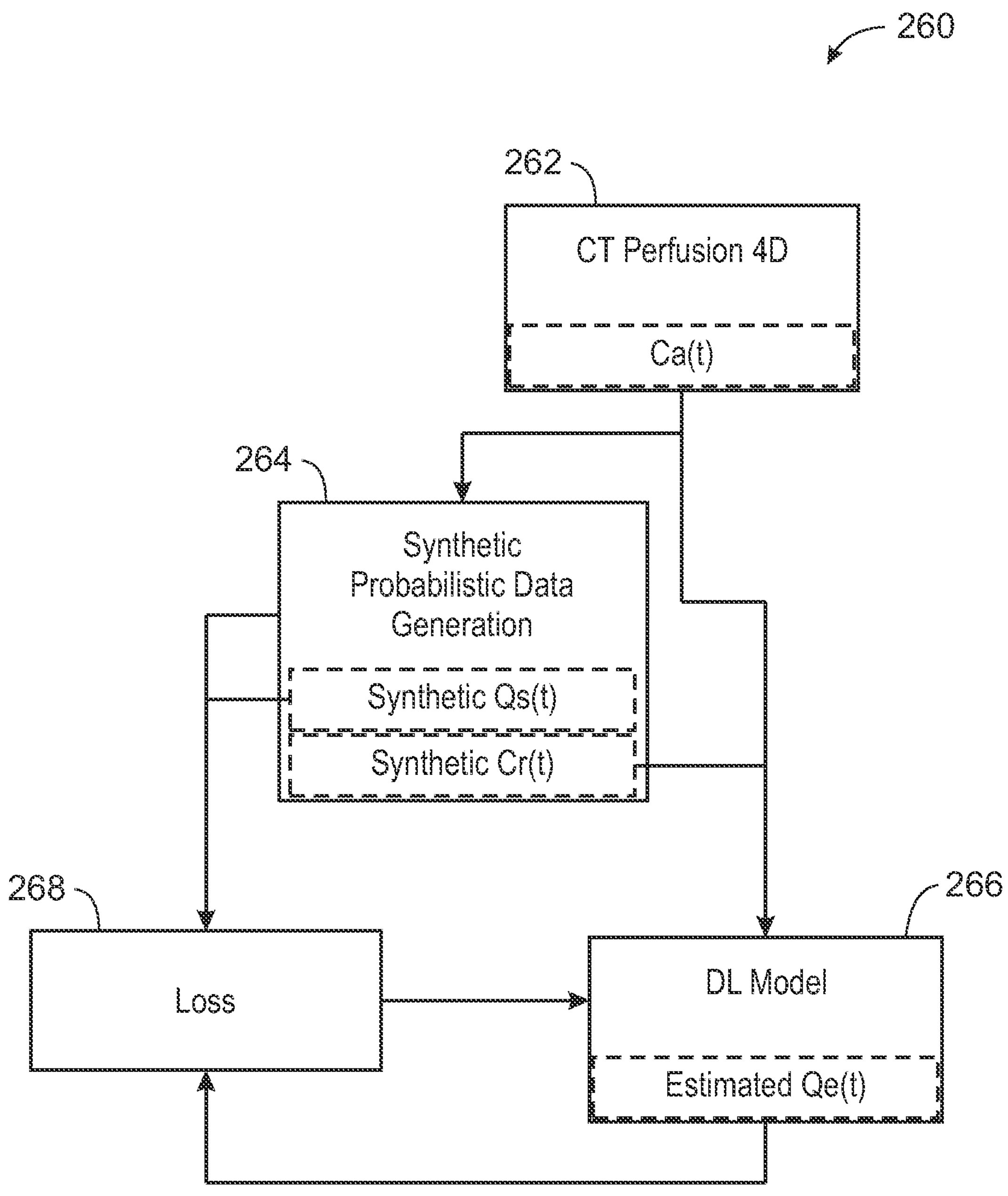
FIG. 6 depicts a flow chart illustrating a method for training a deep learning (DL) model, in accordance with aspects of the present disclosure.

FIG. 6 is a flow chart illustrating a method 260 for training a deep learning model for the deconvolution in the block 230 of FIG. 5. At block 262, an artery signal $C_a(t)$ for an area of tissue may be obtained from the 4D computed tomography perfusion data. At block 264, a synthetic residual impulse function $Q_S(t)$ for the area of tissue may be generated using a ground truth model. An area of tissue used to compute tissue signal may include many capillaries, and the capillary parameters may be described by a probability distribution. Models may be developed to take into account the distribution of capillaries and capillary parameters in tissue. For a defined model with known probability distributions of parameters, a set of residual impulse functions Q(t) may be generated and averaged to obtain the synthetic residue impulse function $Q_S(t)$. Then, a tissue signal $C_r(t)$ may be generated based on Equation (1) using the synthetic residual impulse function $Q_S(t)$ and an artery signal $C_a(t)$. In certain implementations, the tissue signal $C_r(t)$ may be generated using synthetic artery signal $C_a(t)$ data for which ground truth data is known. In certain implementations, the artery signal $C_a(t)$ may be based in part, or derived from, clinical image data (e.g., the 4D computed tomography perfusion data in block 262). In some embodiments, a perturbation (e.g., additive noise) may be added to the tissue signal $C_r(t)$ for the noise, resolution limits, and other image non-idealities in the 4D computed tomography perfusion data, as well as registration errors that may occur during perfusion data acquisitions (e.g., patient movements during acquisition), etc. The generated synthetic residual impulse function $Q_S(t)$ and the tissue signal $C_r(t)$ may be stored (e.g., in the database 170) as training data. At block 266, the arterial signal $C_a(t)$ generated at the block 262 and the generated tissue signal $C_r(t)$ at the block 264 may be input into a deep learning model to calculate an estimated residual impulse function $Q_e(t)$ (e.g., using the predicting component 168), as illustrated in detail in FIG. 7. At block 268, the estimated residual impulse function $Q_e(t)$ and the synthetic residual impulse function $Q_S(t)$ may be used to calculate a loss function, which may be backpropagated to the block 266 to guide the deep learning model training, as illustrated in detail in FIG. 8. For example, the loss function may be used to calculate learnable weights and biases for the processing layers (e.g., hidden layers) in the deep learning model, and the blocks 266 and 268 may be repeated until the value of the loss function is less than a threshold.

Figure 7:
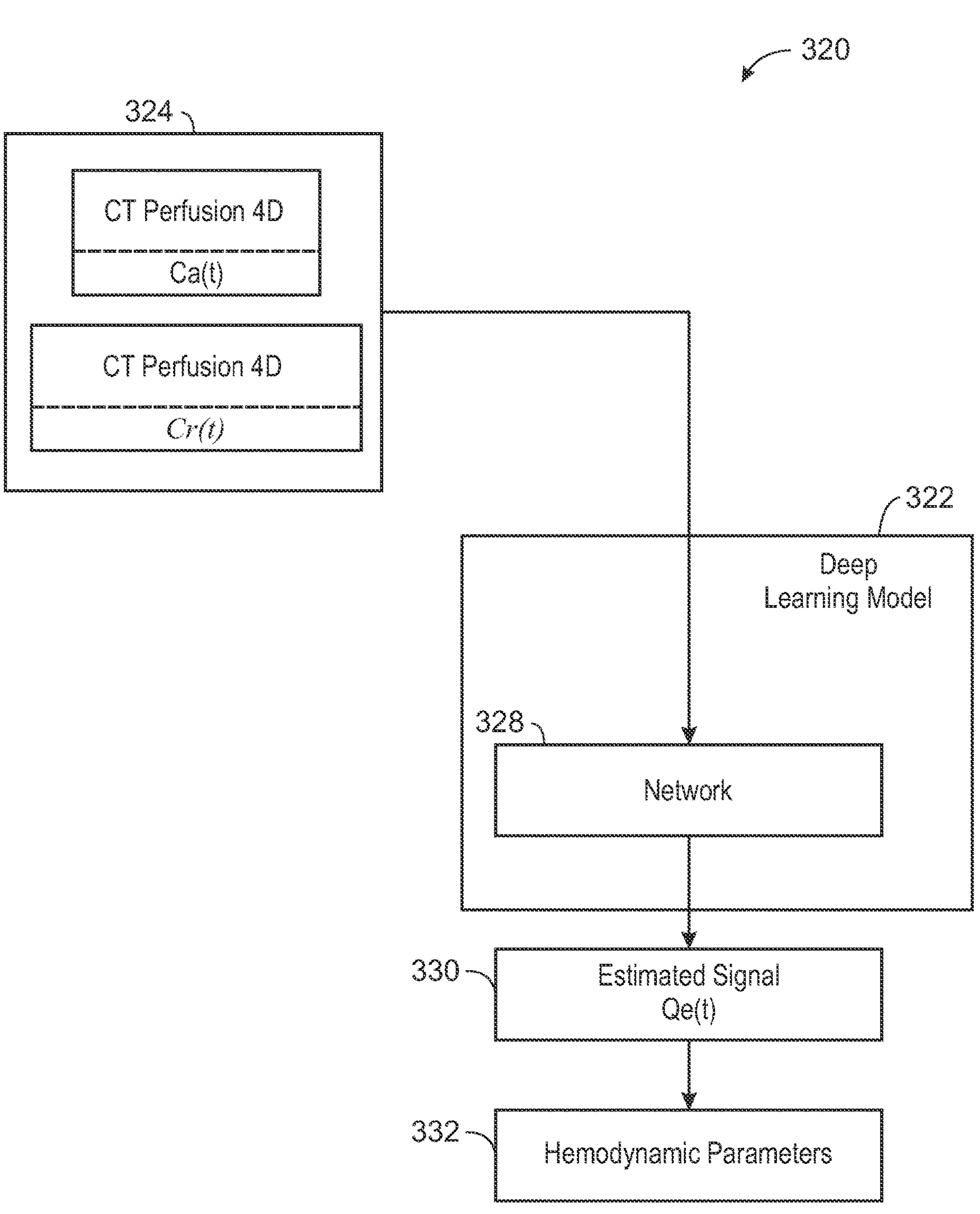
FIG. 7 depicts a flow chart illustrating a method for using a deep learning model to predict an estimated residual impulse function, in accordance with aspects of the present disclosure.

FIG. 7 is a flow chart illustrating a method 320 for using a deep learning model 322 to predict an estimated residue impulse function $Q_e(t)$. At block 324, the arterial signal $C_a(t)$ and the tissue signal $C_r(t)$ obtained from the CT perfusion 4D data may be input into the network (e.g., input layers 54 of the network) of the deep learning model 322 at block 328. At block 330, the deep learning model 322 may output parameters that could be transform to an estimated residual impulse function $Q_e(t)$. At block 332, hemodynamic parameters may be determined by using the estimated residual impulse function $Q_e(t)$ obtained at block 330. Although one deep learning model is illustrated in FIG. 7, multiple deep learning models may be used alone or together to predict the estimated residual impulse function $Q_e(t)$.

Figure 8:
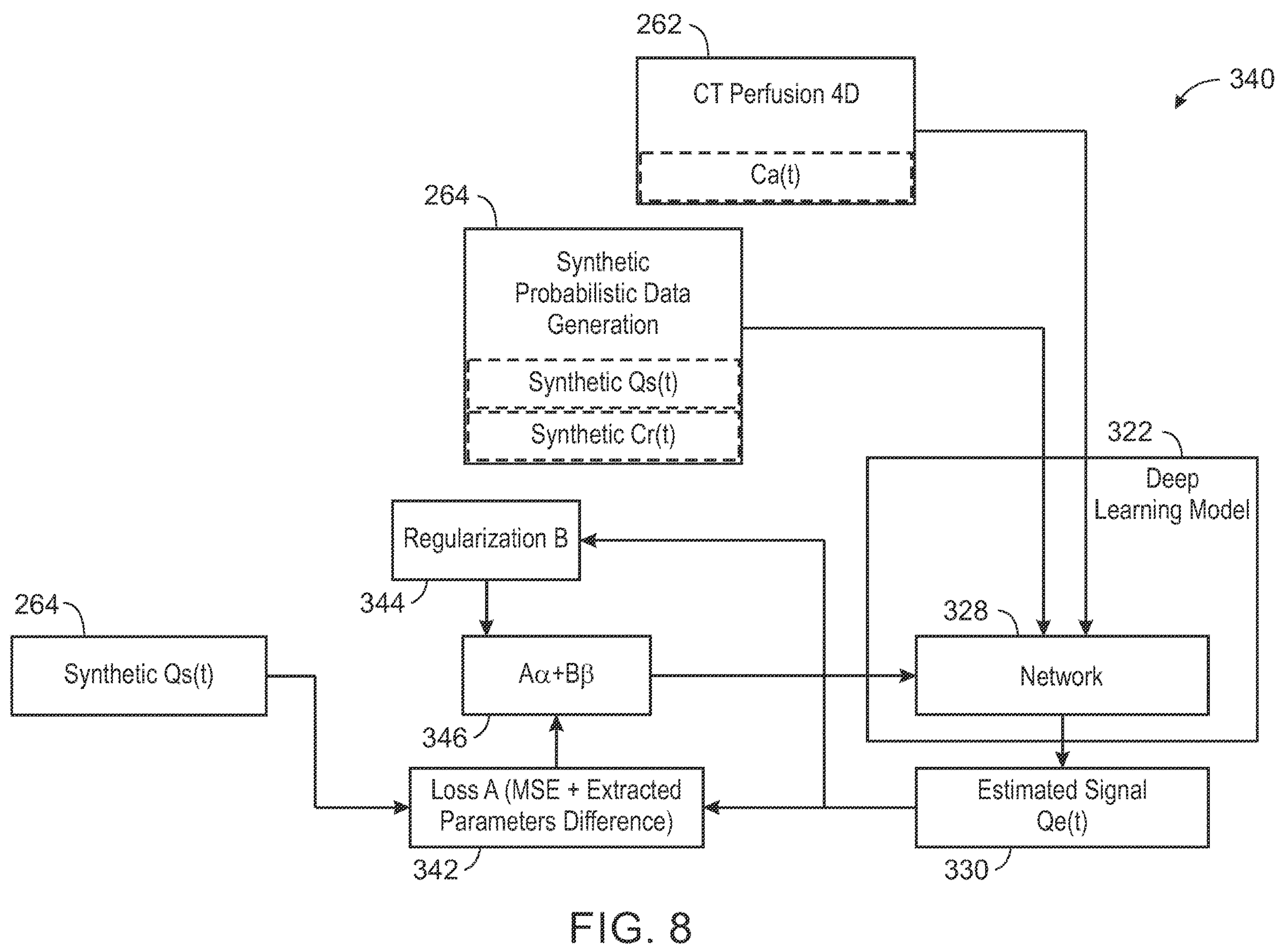
FIG. 8 depicts a flow chart illustrating a method for training the deep learning model of FIG. 7, in accordance with aspects of the present disclosure.

FIG. 8 is a flow chart illustrating a method 340 for training the deep learning model 322 using a loss function. The arterial signal $C_a(t)$ obtained from the CT perfusion 4D data at block 262 and the synthetic tissue signal $C_r(t)$ obtained at block 264 may be input into the network (e.g., input layers 54 of the network) of the deep learning model 322 at block 328. At block 330, the deep learning model 322 may output parameters that could be transform to an estimated residual impulse function $Q_e(t)$. At block 342, the estimated residual impulse function $Q_e(t)$ obtained by the deep learning model 322 at block 330 may be used to calculate various parameters (e.g., hemodynamic parameters) and derive various features, which may be compared with the corresponding parameters and features calculated or derived using the synthetic residual impulse function $Q_S(t)$, and the difference may be used to determine a loss function A, which may be used as a bias to train all or a part of the deep learning model 322. The loss function A may also include the mean squared error (MSE) of the voxel level values or partial line integral values and/or may account for differences involving other image features, such as image gradients or other image statistics. At block 344, the estimated residual impulse function $Q_e(t)$ obtained by the deep learning model 322 at block 330 may be used to determine a regularization bias B, which may be related to the characteristics of the estimated residue impulse function $Q_e(t)$ (e.g., a second order of differentiation of $Q_e(t)$). At block 346, a training weight a (e.g., any real number) may be determined for the loss function A and a training weight R (e.g., any real number) may be determined for the regularization bias B, and the weighted loss function A and the weighted regularization bias B may be backpropagated to the network (e.g., hidden layers 58A, 58B of the network) of the deep learning model 322 to guide the network training. The blocks 328, 330, 342, 344, and 346 may be repeated until the value of the loss function is less than a threshold, and the deep learning training for the deep learning model 322 may be finished. The clinical arterial signal Ca(t) and tissue signal Cr(t) obtained from the computed tomography perfusion 4D data may then be input into the trained deep learning model 322 to determine the estimate residual impulse function $Q_e(t)$. In these embodiments that the perturbation (e.g., additive noise) is added to the tissue signal $C_r(t)$, noises in the output of the trained deep learning model 322 due to image non-idealities in the 4D computed tomography perfusion data or registration errors that may occur during perfusion data acquisitions (e.g., patient movements during acquisition) may be reduced/mitigated since the deep learning model 322 has been trained against the noise, resolution limits, and other image non-idealities in the 4D computed tomography perfusion data as well as the registration errors by adding the perturbation into the training data. The clinical arterial signal Ca(t) and tissue signal Cr(t) may be sampled by multiphase images acquisition, and the samplings of them are not constrained to be equal or regular. In addition, support of samplings are not constrained to be same across application. A fix support may be used for input as minimum acquisition duration. Moreover, signals (e.g., Ca(t), Cr(t)) may be interpolated with a fixed step (e.g., ≤0.5 s).

Figure 9:
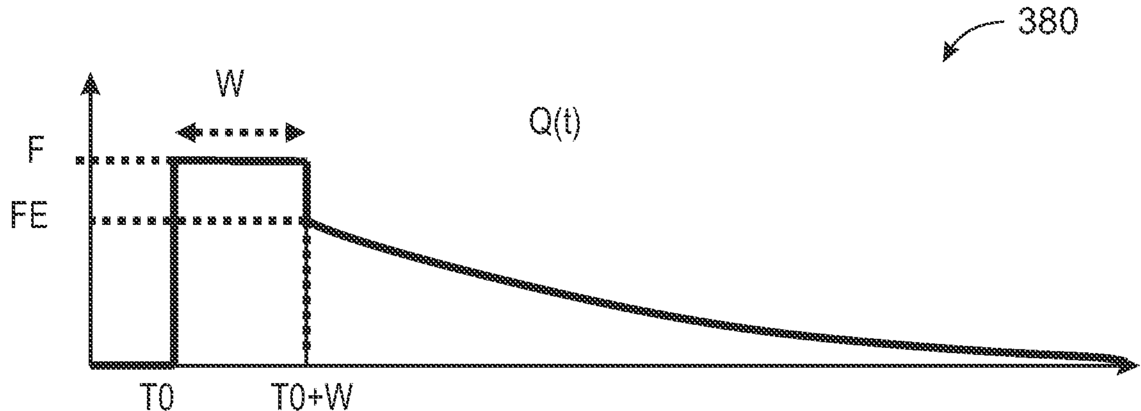
FIG. 9 depicts a ground truth model that may be used for synthetic data generation in FIG. 6, in accordance with aspects of the present disclosure.

FIG. 9 shows an embodiment of a ground truth model 380 that may be used for synthetic data generation in FIG. 6. In the ground truth model 380, the value of the residue impulse function Q(t) is zero before time TO. The residue impulse function Q(t) is equal to the relative flow F at time TO and decreases from the relative flow in extravascular FE after time T0+W, while W is the mean transit time (MTT). In addition, the residue impulse function Q(t) is nonnegative during the acquisition. The above characteristic of the ground truth model 380 may be used to determine the regularization bias B.

Technical effects of the invention include utilizing deep learning (DL) approaches to estimate hemodynamic parameters from four dimensional (4D) computed tomography perfusion data. During a computed tomography acquisition, a series of images are acquired for a region of interest (e.g., a tissue), which include images taken before, during, and after an injection of a contrast agent (e.g., tracer bolus or marking blood with other way (e.g., ASL)) to the region of interest. Deep learning algorithms are trained using synthetic (e.g., simulated) data generated based on the 4D computed tomography perfusion data to obtain a residual impulse function Q(t) of the region of interest. In addition, the deep learning models may be trained to reduce/mitigate the image non-idealities in the 4D computed tomography perfusion data. Neural networks trained in this manner are used to estimate the residual impulse function Q(t) of the region of interest, which is used to determine corresponding hemodynamic parameters of the region of interest, such as blood flow (BF), blood volume (BV), mean transit time (MTT), etc. In certain implementations, one or more neural networks are trained for hemodynamic parameters assessment using synthetic data for which ground truth data is known. In certain implementations, the synthetic data may be based in part, or derived from, clinical image data for which ground truth data is not known or available.

This written description uses examples to disclose the invention, including the best mode, and also to enable any person skilled in the art to practice the invention, including making and using any devices or systems and performing any incorporated methods. However, it should be understood that the present disclosure is not intended to be limited to the particular forms disclosed. Rather, the present disclosure is intended to cover all modifications, equivalents, and alternatives falling within the spirit and scope of the present disclosure as defined by the following appended claims. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The techniques presented and claimed herein are referenced and applied to material objects and concrete examples of a practical nature that demonstrably improve the present technical field and, as such, are not abstract, intangible, or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

The invention claimed is:

1. A method, comprising:

acquiring a set of perfusion data for a region of interest using an imaging system;

obtaining an artery signal from the set of perfusion data;

obtaining a tissue signal from the set of perfusion data; and providing the artery signal and the tissue signal to serve as inputs to one or more neural networks to determine one or more hemodynamic parameters for the region of interest, wherein the one or more neural networks are trained using modified synthetic tissue data generated based on one or more synthetic data modified or combined with one or more clinical perfusion data, wherein training the one or more neural networks comprises:

generating a set of synthetic residual impulse functions for the region of interest based on a defined ground truth model;

obtaining a training artery signal from a training set of perfusion data;

generating a modified synthetic tissue signal based on the set of synthetic residual impulse functions and the training artery signal; and training the one or more neural networks using a signal generated using the modified synthetic tissue signal and the training artery signal, wherein a loss is used as a bias for training the one or more neural networks, and wherein the loss is determined based on a comparison of an estimated residual impulse function output from the one or more neural networks and a first set of parameters derived from the estimated residual impulse function with the set of synthetic residual impulse functions and a second set of parameters derived from the set of synthetic residual impulse functions.

2. The method of claim 1, wherein the set of perfusion data comprises at least one of computed tomography (CT) perfusion data, magnetic resonance imaging (MRI) perfusion data, positron emission tomography (PET) perfusion data, single photon emission computed tomography (SPECT) data, or ultrasound imaging data.

3. The method of claim 1, wherein the one or more synthetic data are generated based on the defined ground truth model.

4. The method of claim 1, wherein the tissue signal is a convolution of the artery signal and a residual impulse function of the region of interest, and wherein the one or more hemodynamic parameters are determined from the residual impulse function.

5. The method of claim 1, comprising correcting non-idealities in the set of perfusion data based on output from the one or more neural networks.

6. The method of claim 1, wherein the one or more hemodynamic parameters comprise at least one of a blood flow (BF), a blood volume (BV), a mean transit time (MTT), or a time to maximum (TMAX).

7. A system comprising:

one or more processors; and memory, accessible by the one or more processors, the memory storing instructions that, when executed by the one or more processors, cause the one or more processors to perform operations comprising:

receiving a set of perfusion data acquired using an imaging system to image a region of interest;

obtaining an artery signal from the set of perfusion data;

obtaining a tissue signal from the set of perfusion data; and providing the artery signal and the tissue signal to serve as inputs to one or more neural networks to determine one or more hemodynamic parameters for the region of interest, wherein the one or more neural networks are trained using modified synthetic tissue data generated based on one or more synthetic data modified or combined with one or more clinical perfusion data, wherein training the one or more neural networks comprises:

generating a set of synthetic residual impulse functions for the region of interest based on a defined ground truth model;

obtaining a training artery signal from a training set of perfusion data;

generating a modified synthetic tissue signal based on the set of synthetic residual impulse functions and the training artery signal; and training the one or more neural networks using a signal generated using the modified synthetic tissue signal and the training artery signal, wherein a regularization is used in a bias used for the training of the one or more neural networks, and wherein the regularization is associated with characteristics of an estimated residual impulse function output from the one or more neural networks.

8. The system of claim 7, wherein the set of perfusion data comprises at least one of computed tomography (CT) perfusion data, magnetic resonance imaging (MRI) perfusion data, positron emission tomography (PET) perfusion data, single photon emission computed tomography (SPECT) data, or ultrasound imaging data.

9. The system of claim 7, wherein the one or more synthetic data are generated based on the defined ground truth model.

10. The system of claim 7, wherein the tissue signal is a convolution of the artery signal and a residual impulse function of the region of interest, and wherein the one or more hemodynamic parameters are determined from the residual impulse function.

11. The system of claim 7, wherein the one or more neural networks are trained to correct image non-idealities in the set of perfusion data.

12. The system of claim 7, wherein the one or more hemodynamic parameters comprise at least one of a blood flow (BF), a blood volume (BV), a mean transit time (MTT), or a time to maximum (TMAX).

13. A method for training one or more neural networks, comprising:

generating a set of synthetic residual impulse functions for a region of interest based on a defined ground truth model;

obtaining an artery signal from a set of perfusion data;

generating a modified synthetic tissue signal based on the set of synthetic residual impulse functions and the artery signal; and training the one or more neural networks using a signal generated using the modified synthetic tissue signal and the artery signal, wherein a loss is used as a bias for the training of the one or more neural networks and wherein the loss is determined based on a comparison of an estimated residual impulse function output from the one or more neural networks and a first set of parameters derived from the estimated residual impulse function with the set of synthetic residual impulse functions and a second set of parameters derived from the set of synthetic residual impulse functions.

14. The method of claim 13, wherein the modified synthetic tissue signal comprises a perturbation related to perturbating of the perfusion data.

15. The method of claim 14, wherein the perturbation is associated with registration errors or with acquisition errors.

16. The method of claim 13, wherein the set of perfusion data comprises at least one of computed tomography (CT) perfusion data, magnetic resonance imaging (MRI) perfusion data, positron emission tomography (PET) perfusion data, single photon emission computed tomography (SPECT) data, or ultrasound imaging data.

17. The method of claim 13, wherein the first set of parameters comprises a first set of hemodynamic parameters and the second set of parameters comprises a second set of hemodynamic parameters.

18. The method of claim 13, wherein a regularization is used in a bias used for the training of the one or more neural networks, and wherein the regularization is associated with characteristics of the estimated residual impulse function.

19. The method of claim 18, wherein the regularization comprises a second order of differentiation of the estimated residual impulse function.

* * * * *